United States Patent [19]
Aldape

[11] Patent Number: 6,021,920
[45] Date of Patent: Feb. 8, 2000

[54] APPARATUS FOR DISPENSING GLOVES AND HAND PROTECTANT EMOLLIENTS

[75] Inventor: Fortunato G. Aldape, Reno, Nev.

[73] Assignee: Microflex Corporation, Reno, Nev.

[21] Appl. No.: 08/987,464

[22] Filed: Dec. 9, 1997

[51] Int. Cl.[7] .................................................. A47F 1/00
[52] U.S. Cl. ............................................ 221/96; 206/233
[58] Field of Search .................................. 221/96, 92, 97, 221/282; 206/233, 581, 225; 312/91, 35; 211/87.01

[56] References Cited

U.S. PATENT DOCUMENTS

| | | | |
|---|---|---|---|
| 2,540,432 | 2/1951 | Evans | 206/233 |
| 3,865,271 | 2/1975 | Gold | 221/96 |
| 4,280,643 | 7/1981 | Cordova et al. | 206/581 |
| 5,035,321 | 7/1991 | Denton | 206/233 |
| 5,299,683 | 4/1994 | Poole | 206/581 |
| 5,439,104 | 8/1995 | Wolska-Klis | 221/96 |
| 5,816,440 | 10/1998 | Shields et al. | 221/45 |

*Primary Examiner*—Kenneth W. Noland
*Attorney, Agent, or Firm*—Evan M. Kent; Stewart L. Gitler

[57] ABSTRACT

Emergency and other personnel needing gloves can retrieve them easily for donning using a glove and hand protectant dispenser. The dispenser includes a backboard having at least one detachable glove dispenser member disposed proximate a first edge of the backboard; and at least one detachable hand protectant disposer proximate a second edge of the backboard.

19 Claims, 1 Drawing Sheet

APPARATUS FOR DISPENSING GLOVES AND HAND PROTECTANT EMOLLIENTS

BACKGROUND OF THE INVENTION

1. Field of the Invention

This invention relates to apparatus for protecting hands; particularly this invention relates to dispensing of gloves and glove related hand preparations; more particularly relates to apparatus for dispensing gloves.

2. State of the Art

Gloves are widely used to protect hands from a wide variety of environmental insults, particularly gloves are use to protect hands from pathenogins, toxic chemicals, and the like. In a great many situations gloves are dispensed under emergency situations to personnel that are unknown at the time the gloves are stocked.

For example, paramedics who use a particular emergency vehicle may all need to use gloves on an emergency basis. The different personnel who may use the emergency vehicle may well have hands in different sizes, or the vehicle may be used to respond to different situations. In such a case, a variety of sizes of gloves and perhaps a variety of kinds or types of gloves should be kept in the emergency vehicle. Moreover, the different personnel who may use a standard set of gloves stocked in an emergency vehicle may have different allergic susceptibilities to material that the gloves are made of. Finally, a particular emergency may dictate the same person using several sets of gloves as the sets become soiled, and particularly as the person using the gloves goes from one victim to the next.

Therefore, a need exists to dispense different size gloves, different types of gloves, and medicaments that may be used to protect the hands from the allergic triggering glove material or may ameliorate any allergic response that may be provoked by the material of the gloves.

SUMMARY OF THE INVENTION

This invention provides emergency and other personnel needing gloves means to retrieve them easily for donning by using a glove and hand protectant dispenser. The dispenser includes a backboard having at least one detachable dispenser box disposed proximate a first edge of the backboard; and at least one detachable hand protectant disposer proximate a second edge of the backboard.

In one embodiment of this invention, an apparatus for dispensing gloves and hand protectants, comprises:

a backboard;

at least one detachable dispenser box disposed proximate a first edge of the backboard; and at least one detachable hand protectant disposer proximate a second edge of the backboard.

In another embodiment of this invention an apparatus for dispensing gloves and hand protectants, comprising:

a backboard;

a plurality of detachable dispenser boxes disposed proximate a first edge of the backboard;

at least one detachable hand protectant disposer, wherein the protectant provides a means of protecting hands from allergic reaction to the material the gloves are made of proximate a second edge of the backboard; and means to affix the backboard to a vertical surface.

BRIEF DESCRIPTION OF THE DRAWING

The FIGURE shows a perspective view of the apparatus of this invention showing how the components fit together.

DETAILED DESCRIPTION OF THE PREFERRED EMBODIMENT

Figure 1:
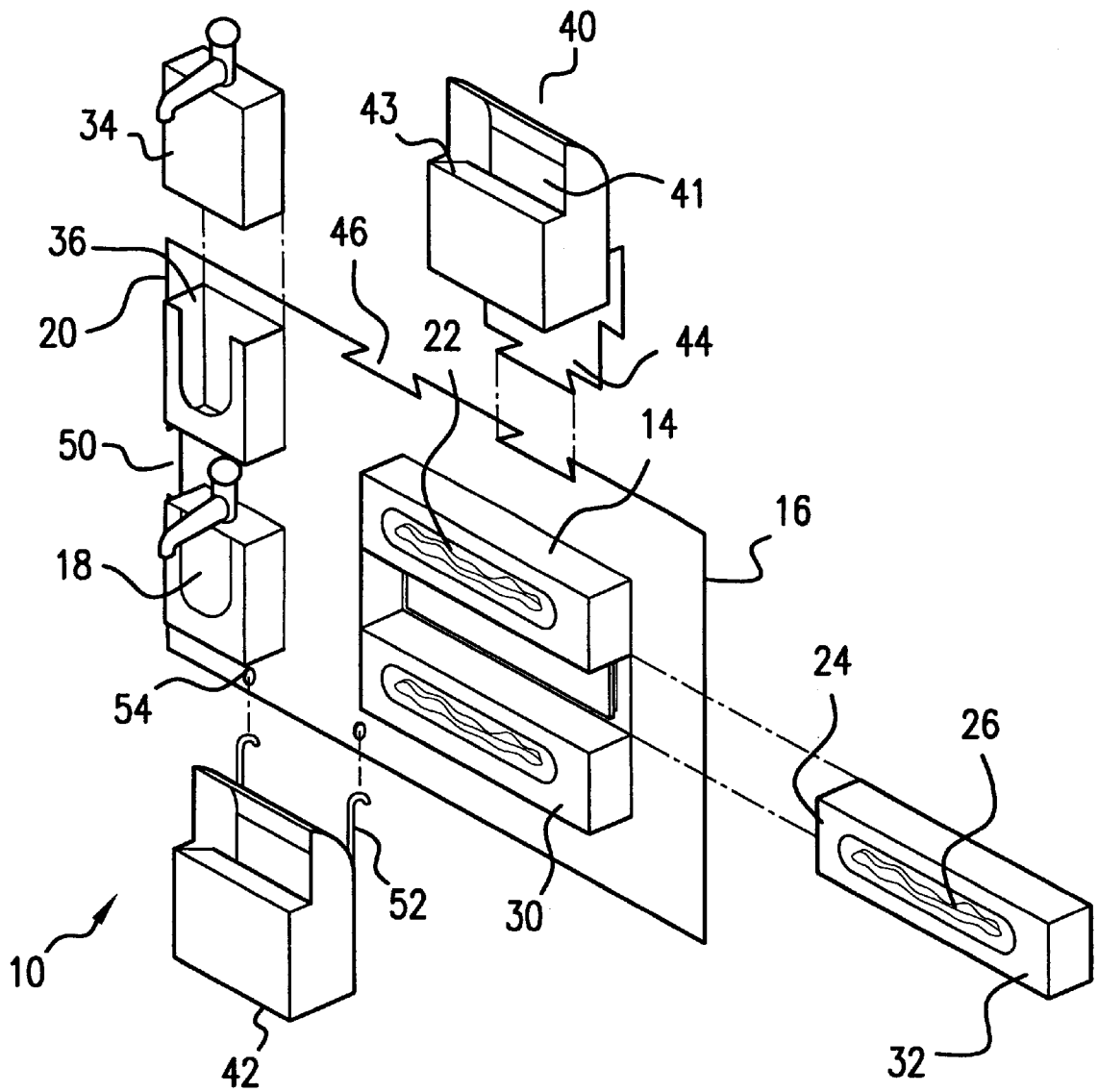

Referring now to the FIGURE, an apparatus for dispensing gloves and hand protectants 10 includes a backboard 12, at least one detachable dispenser box 14 disposed proximate a first edge of the backboard 16, and at least one detachable dispenser of hand protectant 18 disposed proximate a second edge of the backboard 20. The detachable glove dispenser member comprises a hard plastic outer box.

Preferably, the detachable glove dispenser member 14 is made of a resilient plastic or similar material that itself encloses a standard cardboard dispenser box such as those supplied by the manufacturers of gloves, or it may enclose an other conventional means of packaging gloves from the manufacturer. The gloves 22 may be directly loaded into the detachable dispenser box without being exposed to the environment. The glove dispenser member has a first surface 24 defining an elongate aperture 26. The gloves are removed from the member throught the elongate aperture. A second surface opposite the first surface defines a means to attach the dispenser member to the backboard. One preferred way is a mortis and tenon rail attachment means 28, although other equivalent means are well known in the art. The detachable member 32 is shown detached from the backboard. It is reattached by sliding rails that mate with those shown 28. Each detachable member is similarly attached.

It is preferred in the operation of this invention that the glove dispenser include a plurality of glove dispenser boxes 30. They may enclose gloves of different sizes, for example, small, medium and large, or gloves that may be used for different tasks, for example, gloves suitable for emergency medical care, and gloves suitable for use in cleaning toxic materials.

Proximate the second edge of the backboard 20 is a hand protectant dispenser 18. The hand protectant may be, for example, a cream, gel, or lotion that can protect the hand from exposure to direct contact with the glove, or may otherwise soothe the hand and prevent allergic reactions or other undesired effects caused by the gloves. The hand protectant can be dispensed from any conventional means, including pump bottles (as shown), aerosol bottles, squeeze bottles and the like. The hand protectant is detachable, and may be attached to the backboard by any conventional means. One such means is a bottle holder, as shown, although rail arrangements and similar means may be employed. The apparatus preferably also includes a detachable dispenser of a hand conditioner 34 for use after discarding the glove. The hand conditioner may be a moisturizing lotion, or cleansing agent, such as soap or detergent that includes a moisturizing additive. The dispenser containing the hand conditioner is located proximate the dispenser containing the hand protectant. As shown, it is detached from the backboard. For the embodiment shown in the FIGURE, the hand conditioner dispenser is reattached by seating it in a cradle 36. Other conventional means may be utilized to attach the dispenser to the backboard.

It is preferred that the backboard of this invention be affixed to a vertical surface, more preferably the backboard is removably affixed to the vertical surface. A preferred means of affixing the backboard to the vertical surface is by magnetic means, for example, small magnets may be attached to the back of the backboard, or the backboard may be made of magnetized material. Alternatively, the apparatus may be attached to the vertical surface using hook and loop material. In this way, the glove dispenser of this invention can be attached to the out side surface of, for example, an emergency vehicle and used to provide gloves to who ever needs them conveniently on the outside of the vehicle. It will be realized that the backboard may be permanently affixed to structures such as hospital and clinic walls and the like.

In a preferred embodiment a detachable receptacle for sharps 40 and biohazardous materials 42 can be provided. The receptacle has an open top 41 with a downwardly projecting lip 43 to prevent accidental contact with the contents of the receptacle. The top of the receptacle can be locked, if desired. Of course, the design of the receptacle is entirely discretionary, and may be changed to address specific needs. The sharps receptacle is shown attachable with a dove-tail joint 44 into dovetail recesses 46 along the top edge of the backboard. The placement of the sharps receptacle in the drawing is largely to clarify the drawing, but it can be placed on any side of the backboard, and may be placed in substitution for one glove dispenser or an emollient dispenser. A dove-tail is provided in the side of the receptacle for attachment to a dove-tail receptacle 50 in the second edge 20. The placement of the dove-tails as shown is exemplary, and they may be place on the backboard where ever it is the most convenient for use.

The receptacle for bio-hazardous materials 42 is shown attached by an alternative means. Hooks 52 are placed in apertures 54 in the backboard. Again, the position of the placement of the apertures is entirely discretionary with the designer of the unit, and may be modified to address specific needs. Typically, the major difference between the sharps receptacle and the bio-hazardous waste receptacle is that the bio-hazardous waste receptacle is lined with a disposable liner, while the entire container is discarded with the sharps container. It should be appreciated that other waste receptacles can be included in embodiments of this invention.

This invention has been described by reference to specific examples and embodiments which will bring alternative embodiments, modifications, and variations to the minds of those skilled in the art. The appended claims are intended to encompass all such alternatives, modifications, and variations.

I claim:

1. An apparatus for dispensing gloves and hand protectants, comprising:
    a backboard;
    at least one detachable dispenser box disposed proximate a first edge of the backboard, the at least one detachable glove dispenser box having a first surface defining an elongate aperture and a second surface opposite the first surface defining a mortis and tenon rail attachment means; and
    at least one detachable hand protectant disposer proximate a second edge of the backboard.

2. The apparatus of claim 1 wherein the apparatus further comprises a plurality of glove dispenser boxes.

3. The apparatus of claim 1 wherein the hand protectant dispensed comprises a cream.

4. The apparatus of claim 1 wherein the hand protectant dispensed comprises a gel.

5. The apparatus of claim 1 wherein the hand protectant dispensed comprises a lotion.

6. The apparatus of claim 1 further comprising a detachable dispenser of a hand conditioner for use after discarding the glove disposed proximate the disposable dispenser of hand protectant.

7. The apparatus of claim 6 wherein the hand conditioner comprises a moisturizing lotion.

8. The apparatus of claim 6 wherein the hand conditioner comprises cleansing agent with a moisturizing additive.

9. The apparatus of claim 1 wherein the backboard is affixed to a vertical surface.

10. The apparatus of claim 9 wherein the backboard is removably affixed to the vertical surface.

11. The apparatus of claim 10 wherein the backboard is removably affixed to a vertical surface by magnetic means.

12. The apparatus of claim 10 wherein the backboard is removably affixed to a vertical surface by hook and loop material.

13. The apparatus of claim 1 wherein the backboard further comprises a means of disposing of items selected from the group consisting of soiled gloves, used sharps, and bio-hazardous materials.

14. An apparatus for dispensing gloves and hand protectants, comprising:
    a backboard;
    a plurality of detachable dispenser boxes proximate a first edge of the backboard, at least one of the plurality of dispenser boxes having a first surface defining an elongate aperture and a second surface opposite the first surface defining a mortis and tenon rail attachment means;
    at least one detachable hand protectant dispenser, wherein the protectant provides a means of protecting hands from allergic reaction to the material the gloves are made of proximate a second edge of the backboard; and
    means to affix the backboard to a vertical surface.

15. The apparatus of claim 14 wherein the hand protectant dispensed comprises a cream.

16. The apparatus of claim 14 wherein the hand protectant dispensed comprises a gel.

17. The apparatus of claim 14 wherein the hand protectant dispensed comprises a lotion.

18. The apparatus of claim 14 wherein the backboard is removably affixed to the vertical surface.

19. The apparatus of claim 18 wherein the backboard is removably affixed to a vertical surface by magnetic means.

* * * * *